US010501864B2

United States Patent
Sung et al.

(10) Patent No.: US 10,501,864 B2
(45) Date of Patent: Dec. 10, 2019

(54) METHOD FOR MANUFACTURING A PEROVSKITE CRYSTAL STRUCTURE AND APPARATUS FOR MANUFACTURING A PEROVSKITE CRYSTAL STRUCTURE THEREFOR

(71) Applicant: IUCF-HYU (INDUSTRY-UNIVERSITY COOPERATION FOUNDATION HANYANG UNIVERSITY), Seoul (KR)

(72) Inventors: Myung Mo Sung, Seoul (KR); Jang Mi Baek, Suwon-si (KR); Lynn Lee, Ansan-si (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 0 days.

(21) Appl. No.: 15/933,766

(22) Filed: Mar. 23, 2018

(65) Prior Publication Data
US 2018/0216249 A1 Aug. 2, 2018

Related U.S. Application Data

(63) Continuation of application No. PCT/KR2016/010896, filed on Sep. 29, 2016.

(30) Foreign Application Priority Data

Sep. 30, 2015 (KR) ........................ 10-2015-0137484

(51) Int. Cl.
*C30B 7/00* (2006.01)
*C30B 7/06* (2006.01)
(Continued)

(52) U.S. Cl.
CPC ................. *C30B 7/06* (2013.01); *C07F 7/24* (2013.01); *C30B 29/12* (2013.01); *C30B 29/54* (2013.01);
(Continued)

(58) Field of Classification Search
CPC .............. C30B 7/00; C30B 7/14; C30B 29/54
See application file for complete search history.

(56) References Cited

FOREIGN PATENT DOCUMENTS

JP 2009-196845 A 9/2009
JP 2010-013326 A 1/2010
(Continued)

OTHER PUBLICATIONS

Kyeongil Hwang et al., "Toward Large Scale Roll-to-Roll Production of Fully Printed Perovskite Solar Cells", Adv. Mater., Feb. 2015, pp. 1241-1247, vol. 27, Issue 7.
(Continued)

*Primary Examiner* — Robert M Kunemund
(74) *Attorney, Agent, or Firm* — Sughrue Mion, PLLC

(57) ABSTRACT

A method for manufacturing a perovskite crystal structure includes preparing a substrate, disposing a stamp having a roll shape on the substrate, injecting a perovskite precursor solution between the substrate and the stamp, and drying the precursor solution to manufacture a perovskite crystal structure. The stamp rolls in a first direction on the substrate, and the precursor solution is continuously crystallized in the first direction between the substrate and the stamp to manufacture the perovskite crystal structure.

19 Claims, 19 Drawing Sheets

(51) Int. Cl.
- *C07F 7/24* (2006.01)
- *C30B 29/54* (2006.01)
- *H01G 9/00* (2006.01)
- *H01G 9/20* (2006.01)
- *C30B 29/12* (2006.01)
- *H01L 51/00* (2006.01)
- *H01L 51/42* (2006.01)
- *H01L 51/56* (2006.01)

(52) U.S. Cl.
CPC ......... *H01G 9/0029* (2013.01); *H01G 9/2004* (2013.01); *H01L 51/0004* (2013.01); *H01L 51/0007* (2013.01); *H01L 51/4253* (2013.01); *H01L 51/56* (2013.01)

(56) References Cited

FOREIGN PATENT DOCUMENTS

| | | |
|---|---|---|
| KR | 10-2001-0085444 A | 9/2001 |
| KR | 10-2010-0107977 A | 10/2010 |

OTHER PUBLICATIONS

International Search Report of PCT/KR2016/010896 dated Jan. 13, 2017 [PCT/ISA/210].

[Fig. 1]
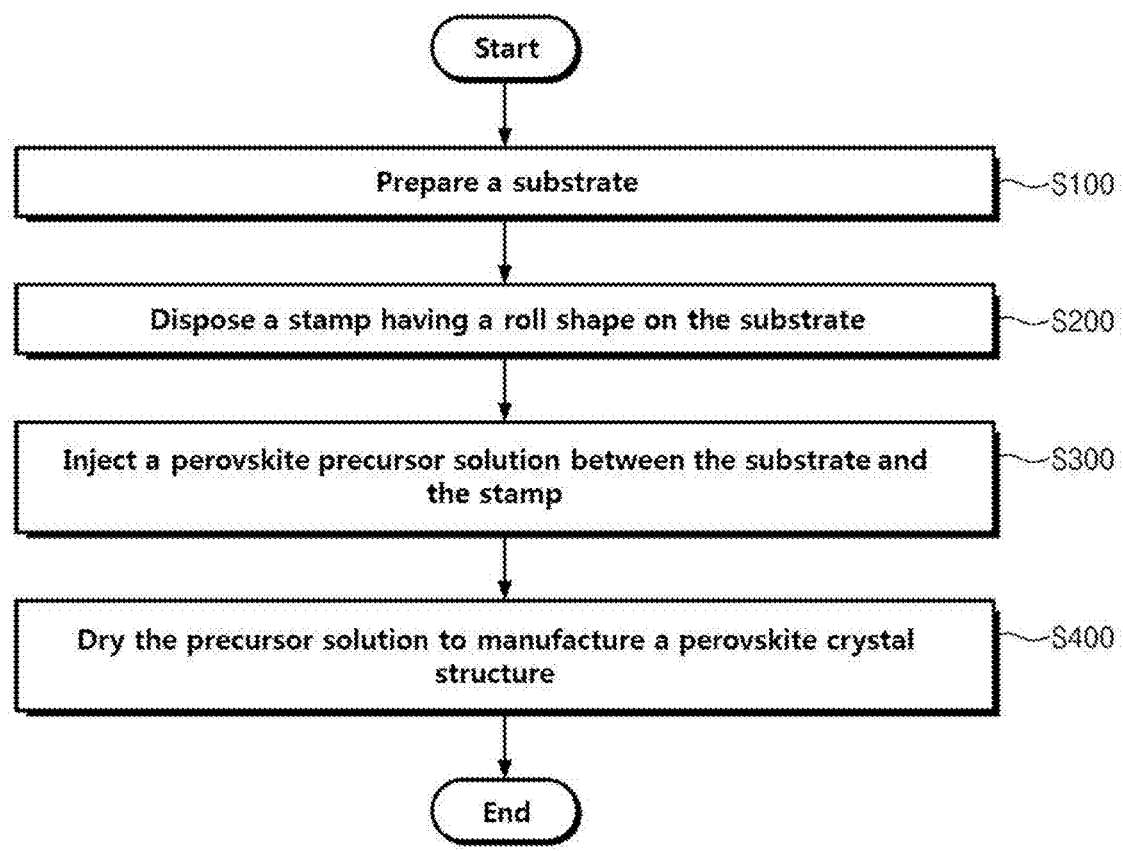

[Fig. 2]
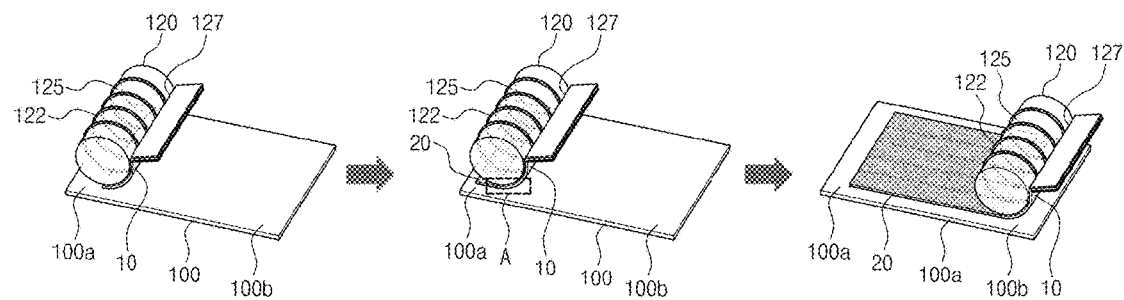

[Fig. 3]
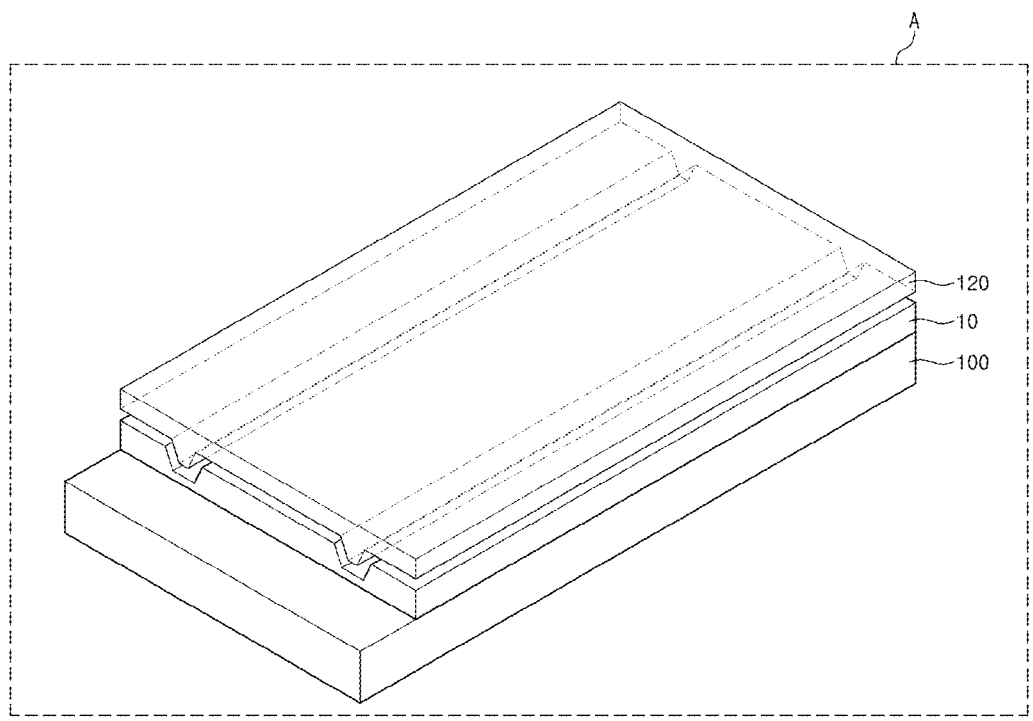

[Fig. 4]
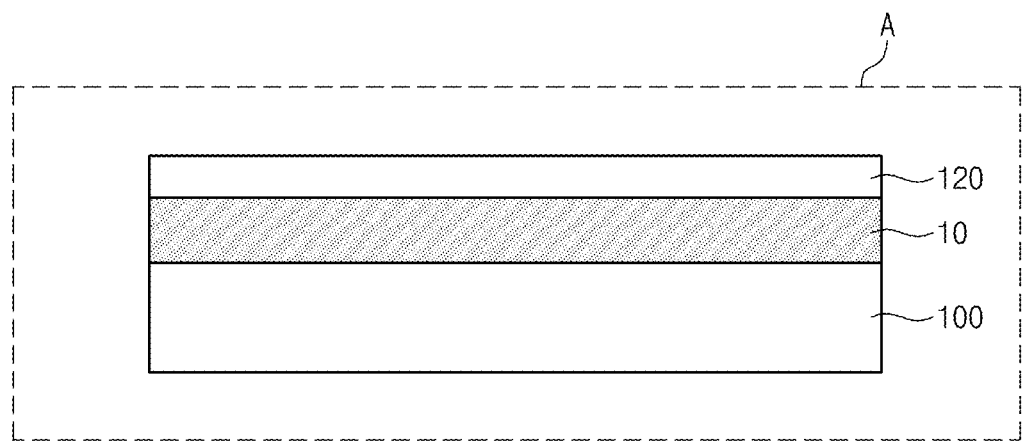

[Fig. 5]
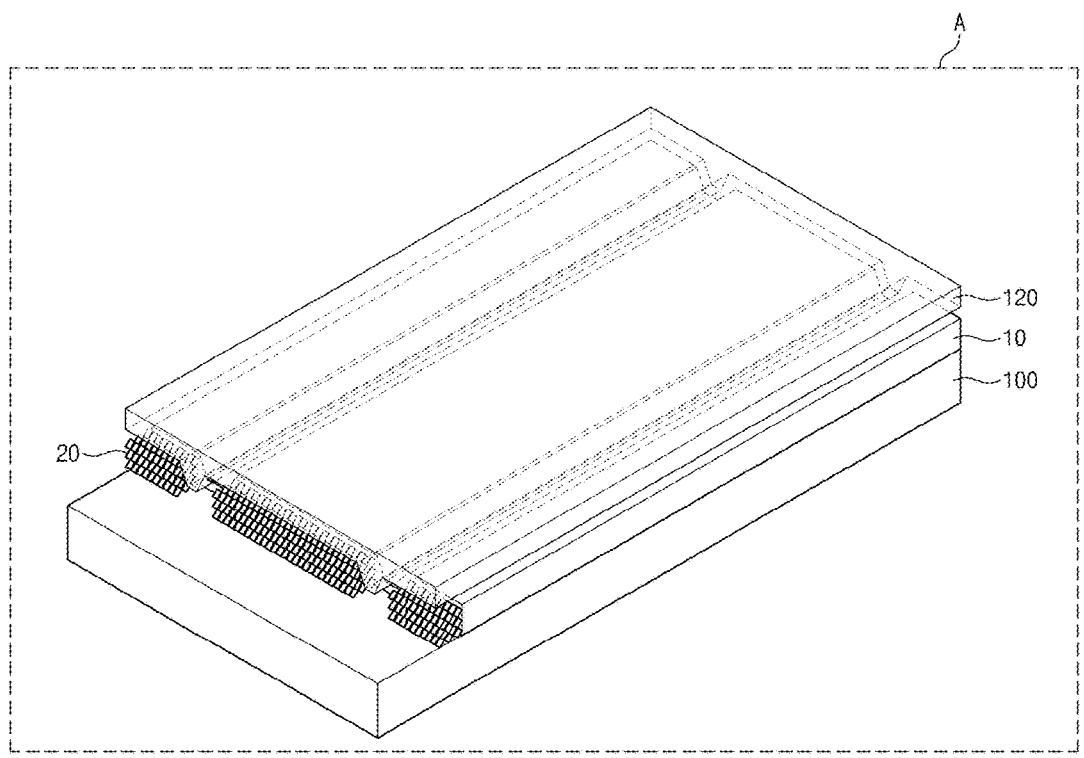

[Fig. 6]
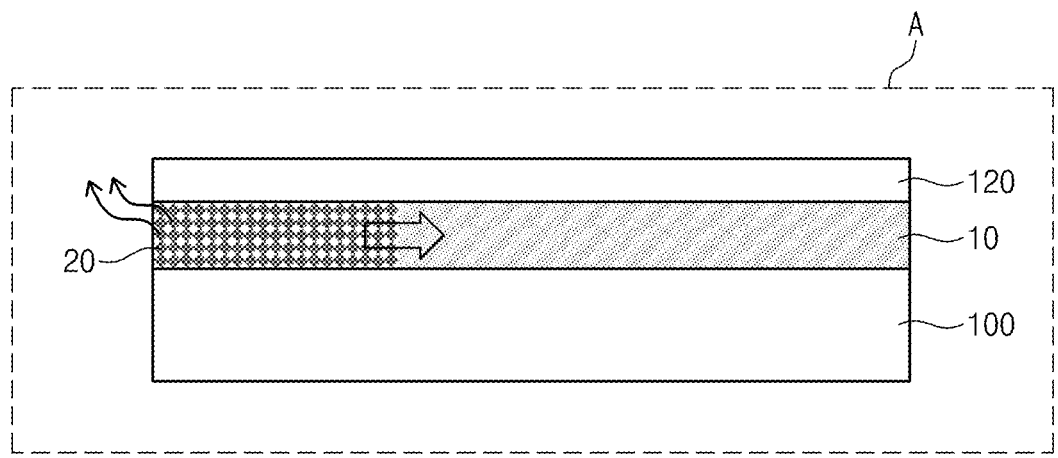

[Fig. 7]
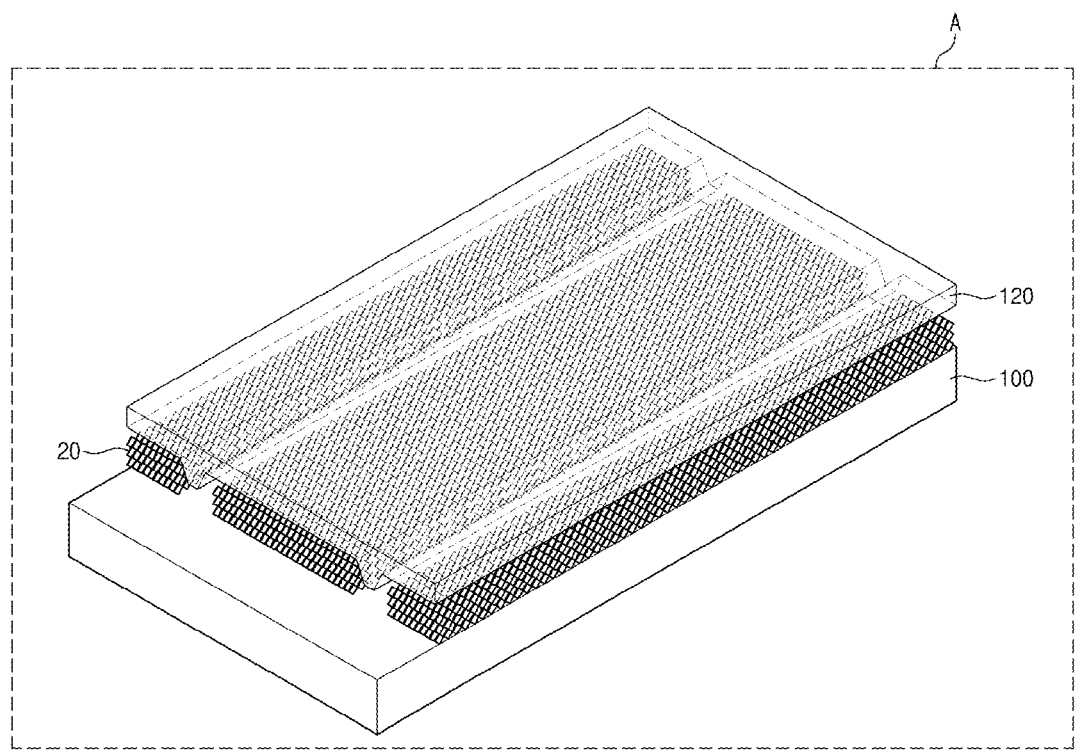

[Fig. 8]
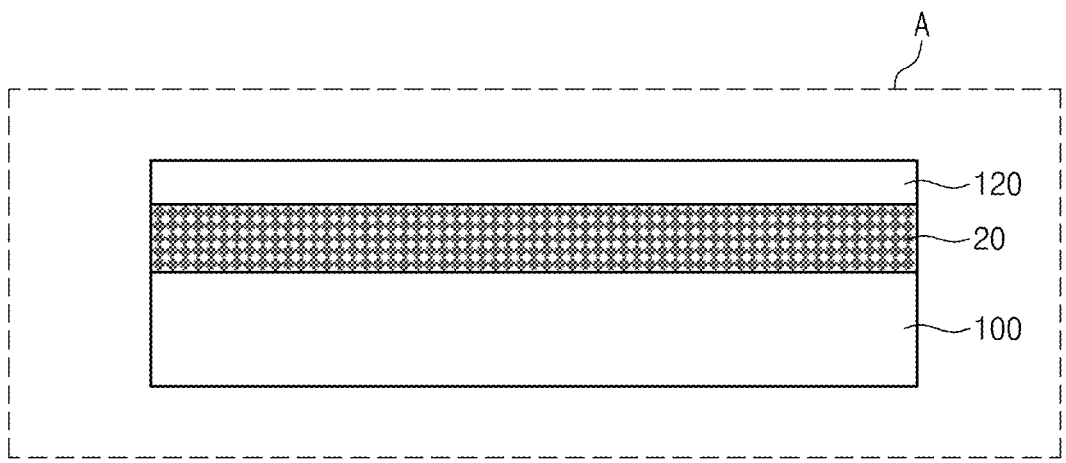

[Fig. 9]
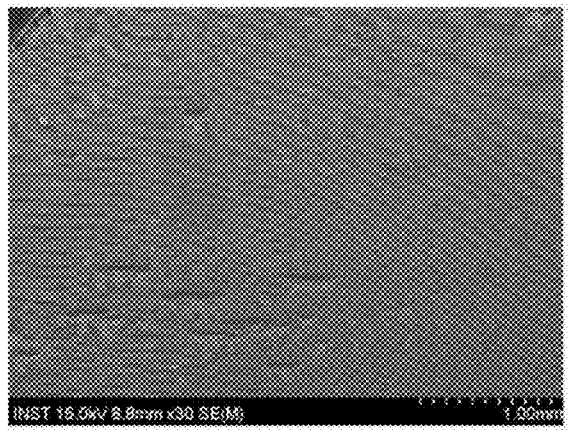

【Fig. 10A】
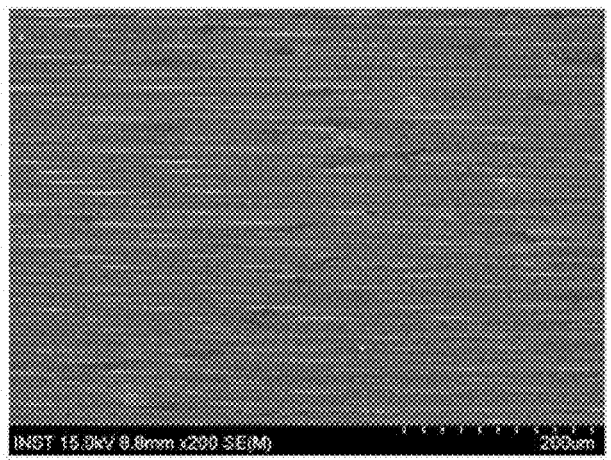
【Fig. 10B】
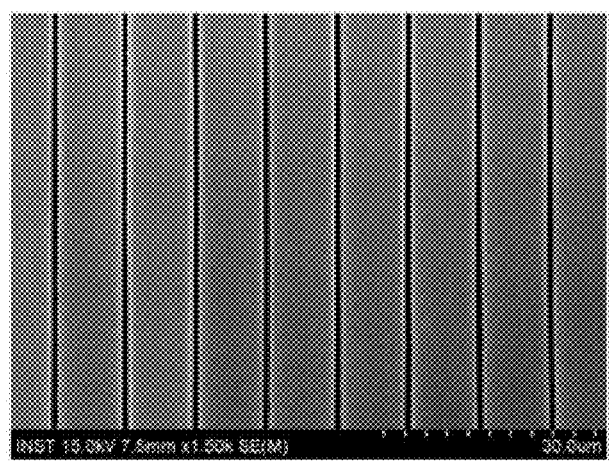

[Fig. 11]
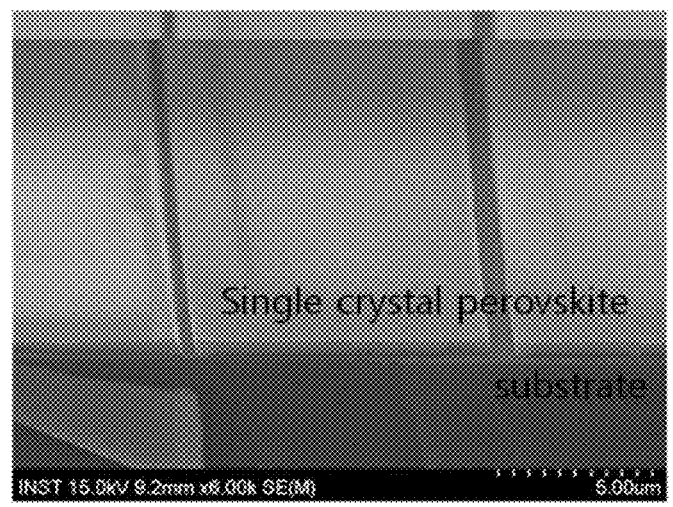

[Fig. 12A]
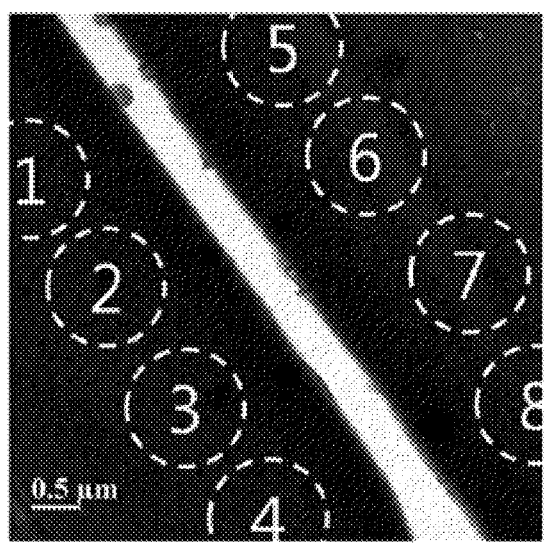
[Fig. 12B]
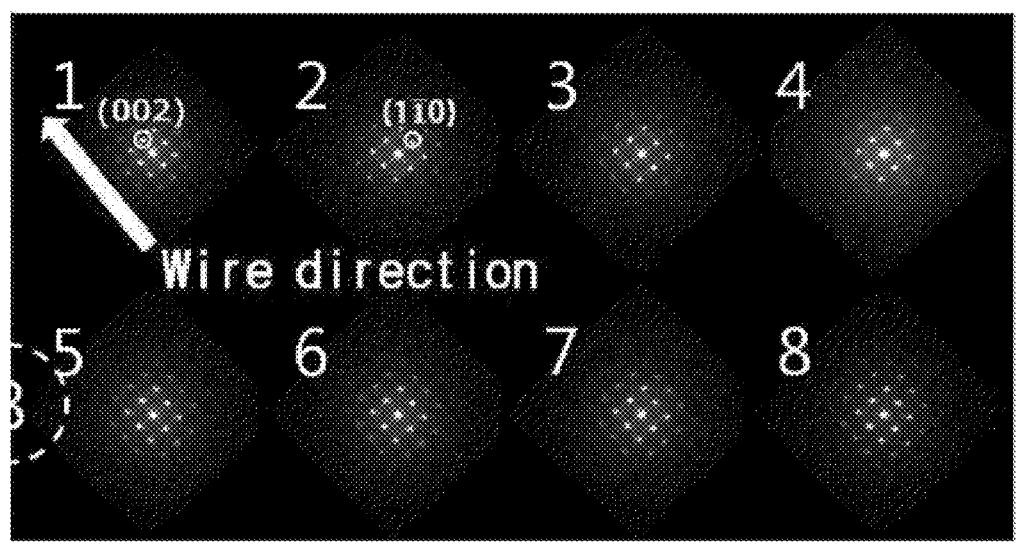

[Fig. 13]
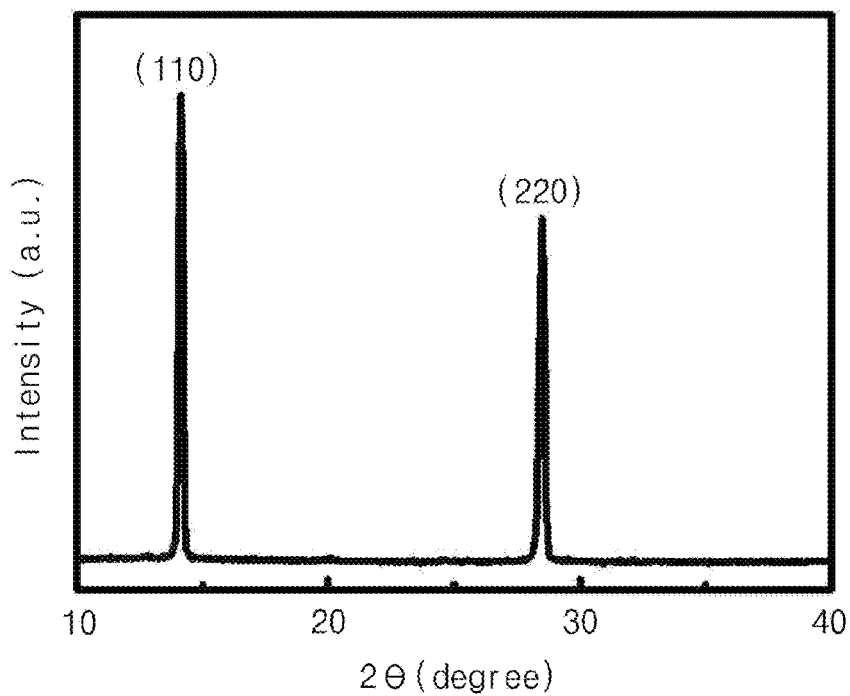

[Fig. 14]
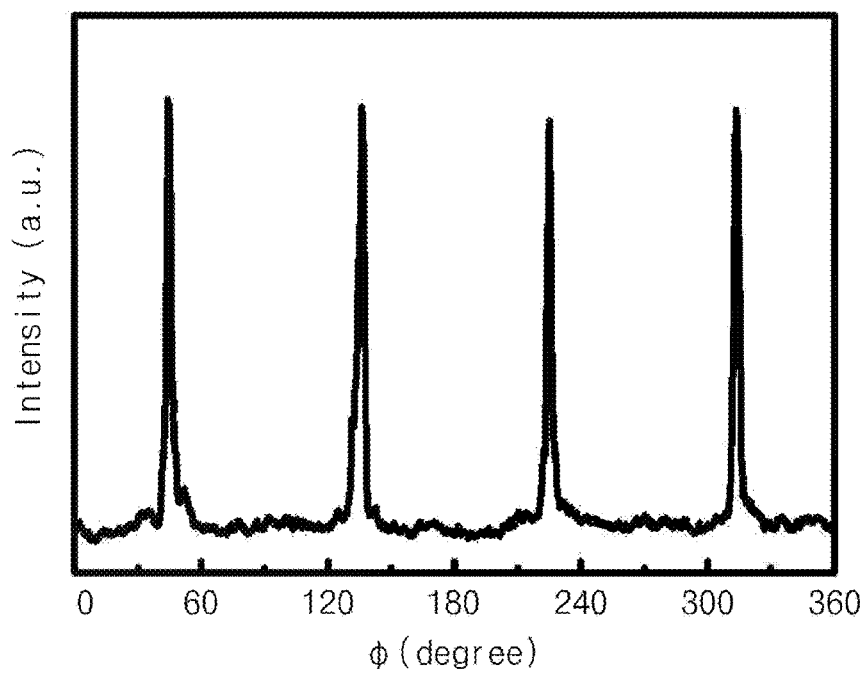

[Fig. 15]
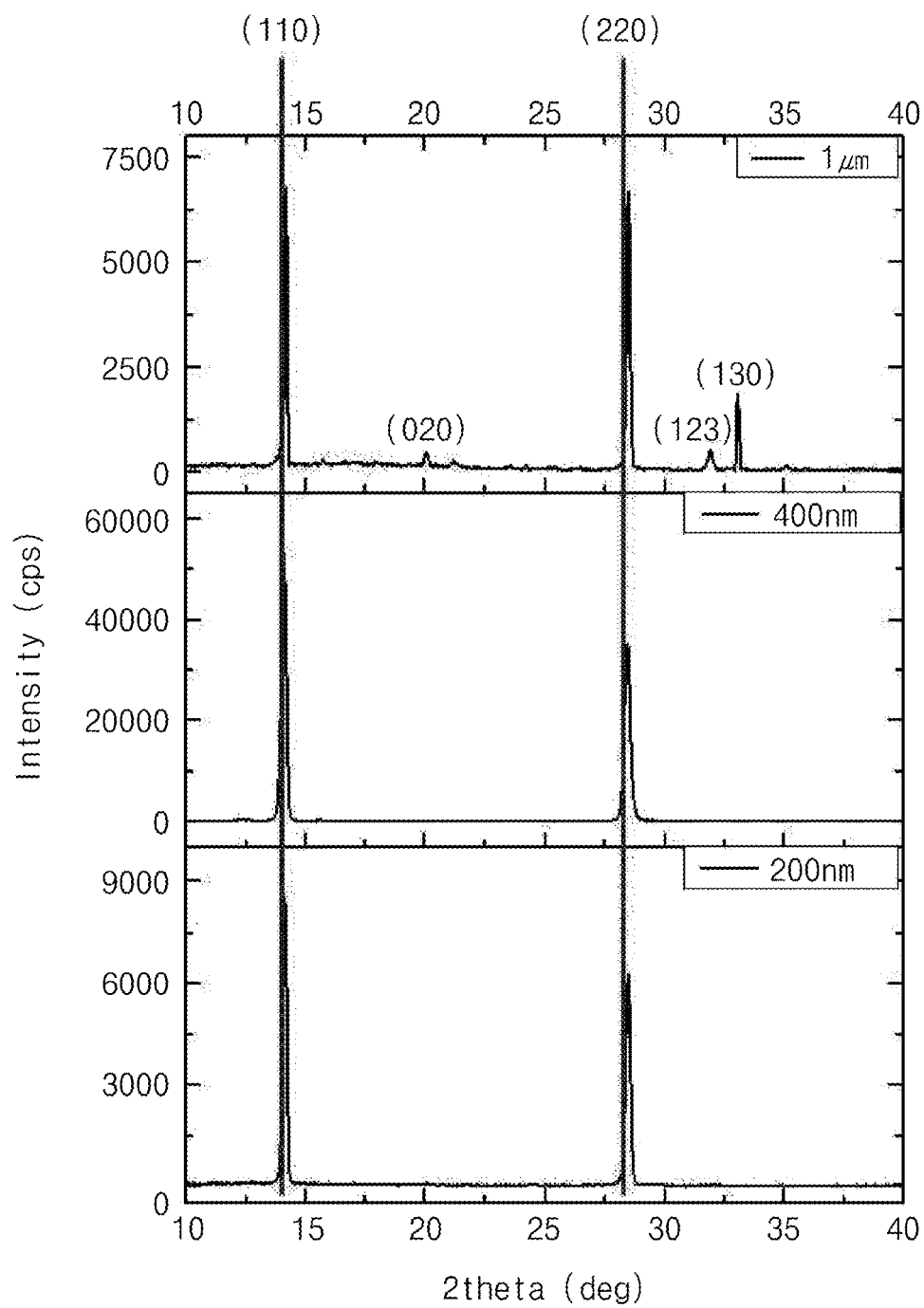

[Fig. 16]
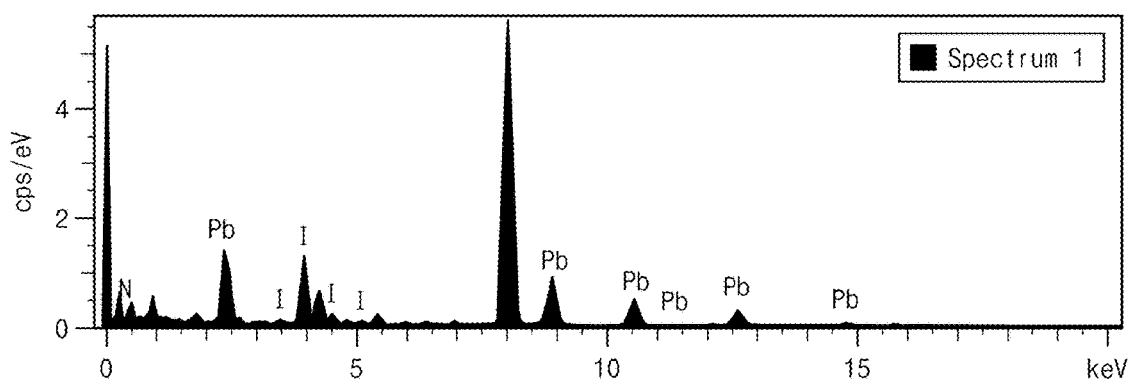

[Fig. 17]
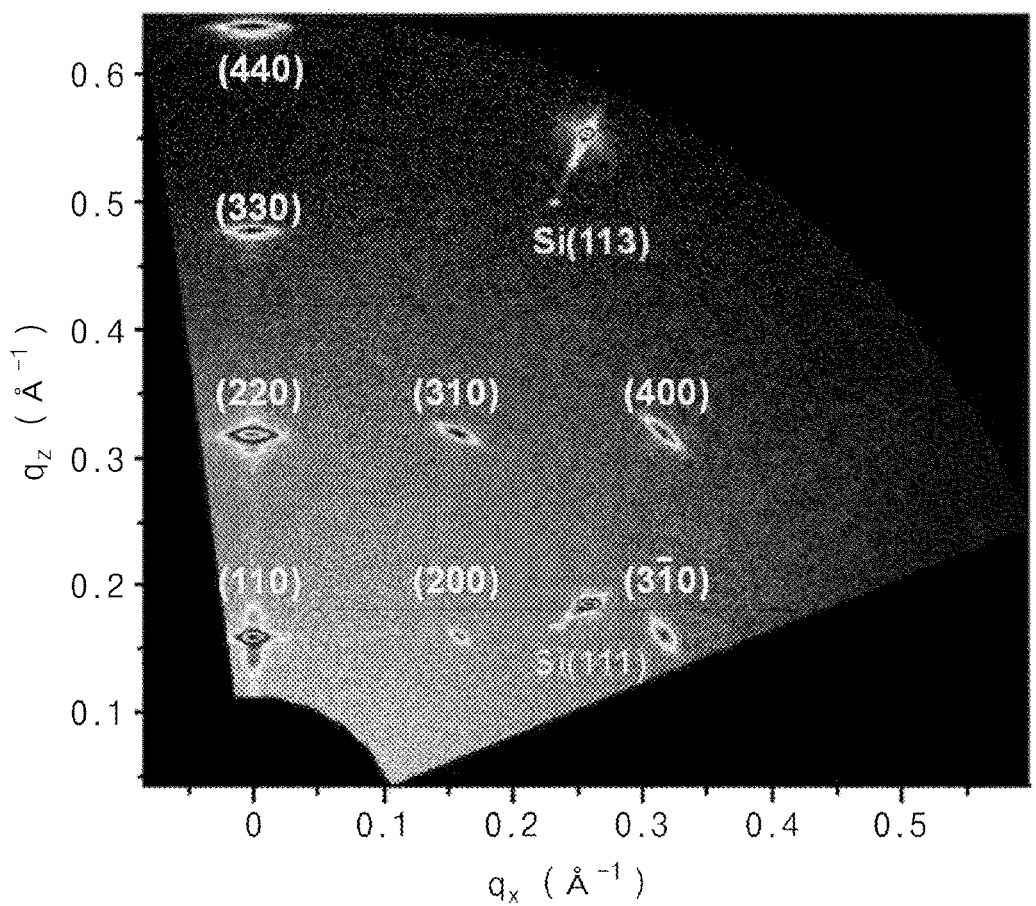

[Fig. 18]
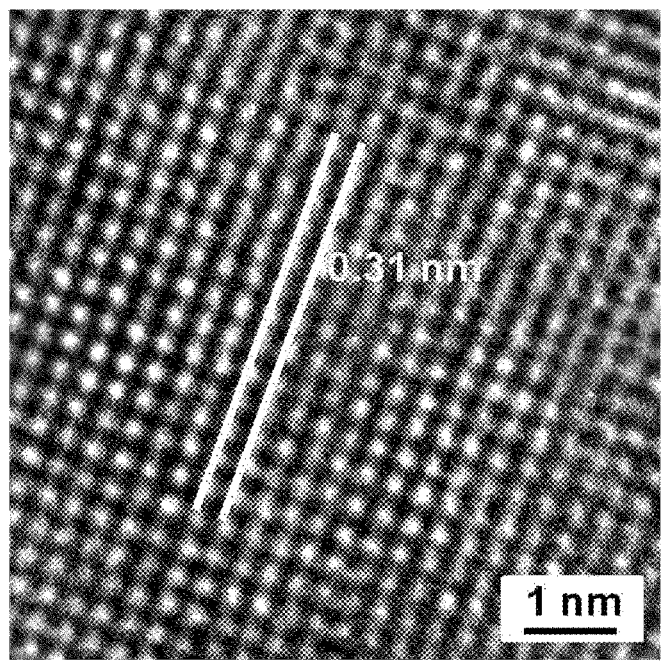

[Fig. 19A]
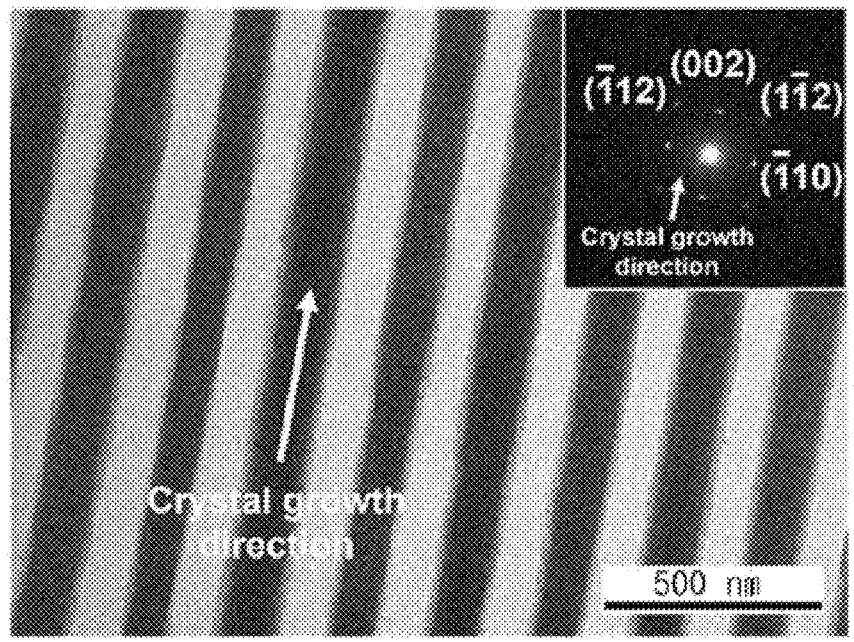
[Fig. 19B]
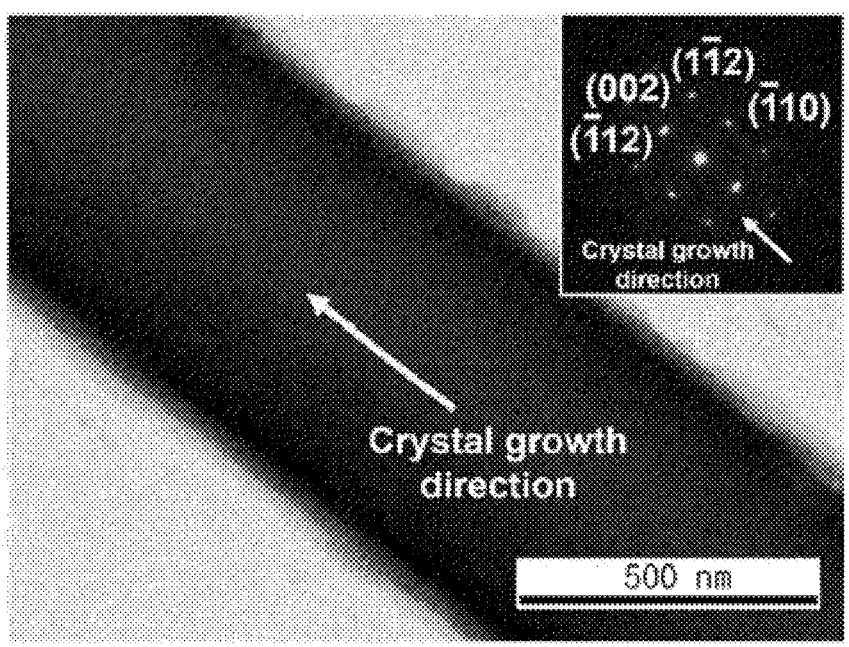

METHOD FOR MANUFACTURING A PEROVSKITE CRYSTAL STRUCTURE AND APPARATUS FOR MANUFACTURING A PEROVSKITE CRYSTAL STRUCTURE THEREFOR

CROSS-REFERENCE TO RELATED APPLICATION

This application is a continuation of pending International Application No. PCT/KR2016/010896, which was filed on Sep. 29, 2016 and claims priority to Korean Patent Application No. 10-2015-0137484, filed on Sep. 30, 2015, in the Korean Intellectual Property Office, the disclosures of which are hereby incorporated by reference in their entireties.

BACKGROUND

1. Field

Embodiments of the inventive concepts relate to a method for manufacturing a perovskite crystal structure and an apparatus for manufacturing a perovskite crystal structure therefor. More particularly, embodiments of the inventive concepts relate to a method for manufacturing a perovskite crystal structure, in which a perovskite precursor solution is supplied into a limited space between a substrate and a roll-shaped stamp rolling on the substrate and a crystal is grown in a direction in which the stamp rolls on the substrate, and an apparatus for manufacturing a perovskite crystal structure therefor.

2. Description of the Related Art

Organic and inorganic hybrid perovskite is a next-generation light absorbing material with excellent optical and electrical characteristics, low cost and ease of use in a process. In particular, since a perovskite organic and inorganic hybrid semiconductor has a basic chemical composition of $ABX_3$, it may be easily synthesized with various kinds of materials and may be used to manufacture a low-cost solar cell. Thus, the perovskite organic and inorganic hybrid semiconductor may emerge as a next-generation solar cell material.

In addition, since the perovskite solar cell is manufactured using a solution process like an organic solar cell, it may be applied to various applications such as large-area and flexible devices, and thus various fields (e.g., laser or a light-emitting electronic device) using the perovskite are actively being studied.

For example, Korean Patent Publication No. KR20140003998A (Applicant: Sungkyunkwan University Research & Business Foundation, Application No. KR20130032089A) discloses a perovskite solar cell which includes a first electrode including a conductive transparent material, a light absorbing layer formed on the first electrode, a hole transport layer formed on the light absorbing layer, and a second electrode formed on the hole transport layer. The light absorbing layer includes a dye having a semiconductor layer and a perovskite structure. Unlike a conventional dye-sensitized solar cell, the perovskite solar cell uses the dye having the perovskite structure, not a ruthenium metal complex, as a photosensitive agent. Thus, the perovskite solar cell may have high energy conversion efficiency and may solve problems a high cost, a long time for dye adsorption and a thick light absorbing layer of a dye-sensitized solar cell using the ruthenium metal complex as a dye.

A method for simplifying processes of manufacturing a perovskite capable of reducing a process time and a process cost and a method for manufacturing a single-crystalline perovskite on a large-area substrate are being studied to apply and commercialize the perovskite in various fields.

SUMMARY

Embodiments of the inventive concepts may provide a method for manufacturing a single-crystalline perovskite crystal structure using a solution process, and an apparatus for manufacturing a perovskite crystal structure therefor.

Embodiments of the inventive concepts may also provide a method for manufacturing a perovskite crystal structure capable of easily adjusting a thickness, and an apparatus for manufacturing a perovskite crystal structure therefor.

Embodiments of the inventive concepts may further provide a method for manufacturing a perovskite crystal structure having a large-area single-crystalline structure, and an apparatus for manufacturing a perovskite crystal structure therefor.

Embodiments of the inventive concepts may further provide a method for manufacturing a perovskite crystal structure capable of reducing a process time and a process cost, and an apparatus for manufacturing a perovskite crystal structure therefor.

In an aspect, a method for manufacturing a perovskite crystal structure may include preparing a substrate, disposing a stamp having a roll shape on the substrate, injecting a perovskite precursor solution between the substrate and the stamp, and drying the precursor solution to manufacture a perovskite crystal structure. The stamp may roll in a first direction on the substrate, and the precursor solution may be continuously crystallized in the first direction between the substrate and the stamp to manufacture the perovskite crystal structure.

In some embodiments, the stamp may roll from a first region of the substrate to a second region of the substrate while rotating about a rotation axis parallel to a second direction perpendicular to the first direction.

In some embodiments, the precursor solution may be supplied onto an outer circumferential surface of the stamp, and the precursor solution may flow along the outer circumferential surface of the stamp so as to be injected between the substrate and the stamp.

In some embodiments, a crystal nucleus may be generated earlier in the precursor solution provided on the first region of the substrate than in the precursor solution provided on the second region of the substrate.

In some embodiments, the drying of the precursor solution may include generating a crystal from the precursor solution and removing a solvent from the precursor solution, by a heating process.

In some embodiments, the stamp may include protrusion portions which are provided on the outer circumferential surface and have loop shapes surrounding the outer circumferential surface.

In some embodiments, the outer circumferential surface of the stamp may include a flat portion between the protrusion portions, and the precursor solution may fill a space between the protrusion portions and between the substrate and the flat portion.

In some embodiments, the space filled with the precursor solution may be adjusted by a distance between the protrusion portions arranged in the second direction on the outer circumferential surface of the stamp and may be adjusted by a distance between the flat portion and the substrate in a third direction perpendicular to the first and second directions.

In some embodiments, a thickness of the perovskite crystal structure formed between the substrate and the flat portion of the stamp may be greater than a thickness of the perovskite crystal structure formed between the substrate and the protrusion portion of the stamp.

In some embodiments, a thickness of the perovskite crystal structure may be determined depending on the distance between the substrate and the flat portion of the stamp.

In some embodiments, a single-crystallinity of the perovskite crystal structure may be adjusted by adjusting a thickness of the perovskite crystal structure.

In some embodiments, the perovskite crystal structure may be a single crystal.

In another aspect, an apparatus for manufacturing a perovskite crystal structure may include a substrate, a stamp having a roll shape on the substrate, and a supply part for supplying a perovskite precursor solution onto an outer circumferential surface of the stamp. The stamp may roll from a first region of the substrate to a second region of the substrate, and the stamp may include protrusion portions which are provided on the outer circumferential surface and have loop shapes surrounding the outer circumferential surface, and a flat portion between the protrusion portions.

In some embodiments, the supply part may move while supplying the precursor solution onto the outer circumferential surface of the stamp, along a direction in which the stamp rolls from the first region to the second region of the substrate.

In some embodiments, the precursor solution provided on the substrate may be crystallized in a direction from the first region toward the second region.

In still another aspect, a method for manufacturing a crystal structure may include providing a precursor solution on a substrate, and drying the precursor solution to manufacture a crystal structure. The precursor solution may be continuously crystallized from a first region of the precursor solution to a second region of the precursor solution.

In some embodiments, the first region of the precursor solution may be provided on the substrate prior to the second region of the precursor solution.

In some embodiments, a single-crystallinity of the crystal structure may be adjusted depending on a thickness of the precursor solution.

In some embodiments, the precursor solution may include a perovskite precursor solution.

In some embodiments, the crystal structure may be a single crystal.

BRIEF DESCRIPTION OF THE DRAWINGS

FIG. 1 is a flowchart illustrating a method for manufacturing a perovskite crystal structure, according to some embodiments of the inventive concepts.

FIG. 2 is a view illustrating a method for manufacturing a perovskite crystal structure, according to some embodiments of the inventive concepts.

FIG. 3 is an enlarged view of a region 'A' of FIG. 2 to illustrate a process in which a perovskite precursor solution is provided between a substrate and a stamp, according to some embodiments of the inventive concepts.

FIG. 4 is a cross-sectional view of FIG. 3 to illustrate the process in which the perovskite precursor solution is provided between the substrate and the stamp, according to some embodiments of the inventive concepts.

FIG. 5 is an enlarged view of the region 'A' of FIG. 2 to illustrate a process in which the perovskite precursor solution provided between the substrate and the stamp is crystallized, according to some embodiments of the inventive concepts.

FIG. 6 is a cross-sectional view of FIG. 5 to illustrate the process in which the perovskite precursor solution provided between the substrate and the stamp is crystallized, according to some embodiments of the inventive concepts.

FIG. 7 is an enlarged view of the region 'A' of FIG. 2 to illustrate a process in which a perovskite crystal structure is manufactured between the substrate and the stamp, according to some embodiments of the inventive concepts.

FIG. 8 is a cross-sectional view of FIG. 7 to illustrate the process in which the perovskite crystal structure is manufactured between the substrate and the stamp, according to some embodiments of the inventive concepts.

FIG. 9 is a scanning electron microscope (SEM) image of a surface of a perovskite crystal structure according to some embodiments of the inventive concepts, which is measured on a scale of a millimeter or more.

FIG. 10A and FIG. 10B show SEM images of a surface of a perovskite crystal structure according to some embodiments of the inventive concepts, which is measured on a scale of a micrometer or more.

FIG. 11 is a SEM image of a cross section of a perovskite crystal structure according to some embodiments of the inventive concepts, which is measured on a scale of a micrometer or more.

FIG. 12A and FIG. 12B show selected area electron diffraction (SAED) images of a perovskite crystal structure according to some embodiments of the inventive concepts.

FIG. 13 is an X-ray diffraction (XRD) graph of a perovskite crystal structure according to some embodiments of the inventive concepts.

FIG. 14 is a graph illustrating an XRD Φ-scan pattern of a perovskite crystal structure according to some embodiments of the inventive concepts.

FIG. 15 is an XRD graph according to a thickness of a perovskite crystal structure according to some embodiments of the inventive concepts.

FIG. 16 is an energy dispersive X-ray spectrometer (EDX) graph of a perovskite crystal structure according to some embodiments of the inventive concepts.

FIG. 17 is a 2D XRD result graph of a perovskite crystal structure according to some embodiments of the inventive concepts.

FIG. 18 is a high-resolution transmission electron microscopy (TEM) image of a perovskite crystal structure according to some embodiments of the inventive concepts.

FIG. 19A and FIG. 19B show SEM images for explaining crystallization of a perovskite crystal structure according to some embodiments of the inventive concepts.

DETAILED DESCRIPTION OF THE EMBODIMENTS

The inventive concepts will now be described more fully hereinafter with reference to the accompanying drawings, in which exemplary embodiments of the inventive concepts are shown. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts.

It will be understood that when an element such as a layer, region or substrate is referred to as being "on" another element, it can be directly on the other element or intervening elements may be present. In addition, in the drawings, the thicknesses of layers and regions are exaggerated for clarity.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concepts explained and illustrated herein include their complementary counterparts. As used herein, the term "and/or" includes any and all combinations of one or more of the associated listed items.

The terminology used herein is for the purpose of describing particular embodiments only and is not intended to limit the invention. As used herein, the singular terms "a", "an" and "the" are intended to include the plural forms as well, unless the context clearly indicates otherwise. It will be further understood that the terms "comprises", "comprising", "includes", "including", "have", "has" and/or "having" when used herein, specify the presence of stated features, integers, steps, operations, elements, and/or components, but do not preclude the presence or addition of one or more other features, integers, steps, operations, elements, components, and/or groups thereof. Furthermore, it will be understood that when an element is referred to as being "connected" or "coupled" to another element, it may be directly connected or coupled to the other element or intervening elements may be present.

In addition, in the present specification, a term "a single-crystallinity" means a ratio of a single crystal having the same crystal growth direction to the whole.

Furthermore, in explanation of the present invention, the descriptions to the elements and functions of related arts may be omitted if they obscure the subjects of the inventive concepts.

FIG. 1 is a flowchart illustrating a method for manufacturing a perovskite crystal structure, according to some embodiments of the inventive concepts, and FIG. 2 is a view illustrating a method for manufacturing a perovskite crystal structure, according to some embodiments of the inventive concepts. FIGS. 3, 5 and 7 are enlarged views of a region 'A' of FIG. 2, and FIGS. 4, 6 and 8 are cross-sectional views of FIGS. 3, 5 and 7, respectively.

Referring to FIGS. 1 to 8, a substrate 100 is prepared (S100). A kind of the substrate 100 is not limited to a specific kind. The substrate 100 may be a metal substrate, a plastic substrate, a silicon semiconductor substrate, a compound semiconductor substrate, or a glass substrate. The substrate 100 may be flexible.

A stamp 120 having a roll shape may be disposed on the substrate 100 (S200). The stamp 120 may include protrusion portions 122 provided on an outer circumferential surface of the stamp 120 and having loop shapes surrounding the outer circumferential surface, and a flat portion 125 between the protrusion portions 122. In addition, a supply part 127 may be located on the outer circumferential surface of the stamp 120. The supply part 127 may supply a perovskite precursor solution 10 onto the outer circumferential surface of the stamp 120.

As illustrated in FIG. 2, the stamp 120 may roll on the substrate 100 in a first direction. In other words, the stamp 120 may roll from a first region 100a of the substrate 100 to a second region 100b of the substrate 100 while rotating about an rotation axis parallel to a second direction perpendicular to the first direction. The supply part 127 may also move in the direction, in which the stamp 120 rolls from the first region 100a to the second region 100b of the substrate 100, while supplying the precursor solution 10 onto the outer circumferential surface of the stamp 120.

The perovskite precursor solution 10 may be injected between the substrate 100 and the stamp 120 (S300). As described above, the supply part 127 may also move in the direction, in which the stamp 120 rolls from the first region 100a to the second region 100b of the substrate 100, while supplying the precursor solution 10 onto the outer circumferential surface of the stamp 120. The precursor solution 10 supplied to the outer circumferential surface of the stamp 120 through the supply part 127 may flow along the outer circumferential surface of the stamp 120 to fill a space between the substrate 100 and the stamp 120.

As described above, the outer circumferential surface of the stamp 120 may include the flat portion 125 between the protrusion portions 122. When the stamp 120 rolls from the first region 100a to the second region 100b of the substrate 100, the protrusion portions 122 of the stamp 120 may come in contact with the substrate 100 but the flat portion 125 of the stamp 120 may not come in contact with the substrate 100. Thus, a space may be generated between the protrusion portions 122 of the stamp 120 and between the substrate 100 and the flat portion 125.

As illustrated in FIGS. 3 and 4, the precursor solution 10 supplied onto the outer circumferential surface of the stamp 120 from the supply part 127 may flow along the outer circumferential surface to fill the space generated between the protrusion portions 122 of the stamp 120 and between the substrate 100 and the flat portion 125. A size of the space filled with the precursor solution 10 may be adjusted by a distance between the protrusion portions 122 arranged on the outer circumferential surface of the stamp 120 in the second direction. In addition, the size of the space may be adjusted by a distance between the flat portion 125 and the substrate 100 in a third direction perpendicular to the first and second directions or a distance from the flat portion 125 to a top surface of the protrusion portion 122 in the third direction.

The precursor solution 10 filling the space generated between the protrusion portions 122 of the stamp 120 and between the substrate 100 and the flat portion 125 may be dried to manufacture a perovskite crystal structure 20 (S400). The method of drying the precursor solution 10 filling the space may include removing a solvent from the precursor solution 10 by a heating process. A shape or kind of a heating unit used in the heating process is not limited to a specific shape or kind. For example, the heating unit may be a heater, a hot plate, or a heating coil. According to an embodiment, the heating unit used in the heating process may be the hot plate. According to an embodiment, a temperature of the heating unit may be maintained at 150 degrees Celsius or more.

As described above, the precursor solution 10 may fill the space generated between the protrusion portions 122 of the stamp 120 and between the substrate 100 and the flat portion 125 along the direction in which the stamp 120 rolls from the first region 100a to the second region 100b of the substrate 100. Thus, as illustrated in FIGS. 5 and 6, the precursor solution 10 filling the space provided on the first region 100a of the substrate 100 may be first dried, and then, the precursor solution 10 filling the space provided on the second region 100b may be dried. When the solvent is removed by drying the precursor solution 10, a crystal nucleus may be generated in the precursor solution 10. In other words, the crystal nucleus may be generated earlier in the precursor solution 10 provided on the first region 100a of the substrate 100 than in the precursor solution 10 provided on the second region 100b of the substrate 100.

Thus, as illustrated in FIGS. 7 and 8, crystallization may continuously proceed from the crystal nucleus generated in the precursor solution 10 provided on the first region 100a to the precursor solution 10 provided on the second region 100b of the substrate 100, and thus the perovskite crystal structure 20 may be manufactured. In other words, the precursor solution 10 may be continuously crystallized in the space, which is generated between the protrusion portions 122 of the stamp 120 and between the substrate 100 and the flat portion 125, in the first direction, and thus the perovskite crystal structure 20 may be manufactured. Thus, a single-crystallinity of the perovskite crystal structure 20 may be improved. In an embodiment, the perovskite crystal structure 20 may be a single crystal.

As described above, the size of the space filled with the precursor solution 10 may be adjusted by the distance between the protrusion portions 122 disposed on the outer circumferential surface of the stamp 120 and/or the distance between the flat portion 125 and the substrate 100. Thus, a thickness of the perovskite crystal structure 20 manufactured by drying the precursor solution 10 provided in the space may be adjusted by the distance between the flat portion 125 of the stamp 120 and the substrate 100 or the distance from the flat portion 125 to the top surface of the protrusion portion 122. According to an embodiment, the thickness of the perovskite crystal structure 20 formed between the flat portion 125 of the stamp 120 and the substrate 100 may be greater than a thickness of the perovskite crystal structure 20 formed between the protrusion portion 122 of the stamp 120 and the substrate 100.

In addition, the single-crystallinity of the perovskite crystal structure 20 may be adjusted by adjusting the thickness of the perovskite crystal structure 20. In an embodiment, the thickness of the perovskite crystal structure 20 may be 400 nm or less. If the thickness of the perovskite crystal structure 20 is greater than 400 nm, the single-crystallinity in the perovskite crystal structure 20 may be reduced.

If a single-crystalline perovskite is manufactured using a conventional spin-coating or spray-coating method unlike the aforementioned embodiments of the inventive concepts, it is difficult to manufacture a single-crystalline perovskite which has a large area and is uniform. A poly-crystalline perovskite manufactured by the spin-coating or spray-coating method may include a lot of trap sites, and a carrier lifetime of the poly-crystalline perovskite may be shorter than that of a single-crystalline perovskite. Thus, if a device is manufactured using the poly-crystalline perovskite, an efficiency of the device may be reduced and stability of the device may be deteriorated.

However, according to the aforementioned embodiments of the inventive concepts, the stamp 120 having the roll shape may be disposed on the substrate 100, and the perovskite precursor solution 10 may be provided between the substrate 100 and the stamp 120 while the stamp 120 rolls from the first region 100a to the second region 100b of the substrate 100. The stamp 120 may include the protrusion portions 122 provided on the outer circumferential surface of the stamp 120 and the flat portion 125 between the protrusion portions 122. The protrusion portions 122 may have the loop shapes surrounding the outer circumferential surface of the stamp 120. The precursor solution 10 may be provided into the space generated between the protrusion portions 122 of the stamp 120 and between the substrate 100 and the flat portion 125. The crystal nucleus may be generated in the precursor solution 10 provided on the first region 100a of the substrate 100, and then, a crystal may be grown from the crystal nucleus generated in the precursor solution 10 provided on the first region 100a to manufacture the perovskite crystal structure 20 in the single-crystalline state.

In addition, according to the embodiments of the inventive concepts, the single-crystalline perovskite crystal structure 20 may be manufactured the solution process (e.g., a liquid process). Moreover, after the precursor solution 10 is supplied into a limited space by the stamp 120, the perovskite crystal structure 20 may be manufactured by a simple process of quickly drying the precursor solution 10 by heating. Thus, a process time and a process cost required to manufacture the single-crystalline perovskite crystal structure 20 may be reduced, and the single-crystalline perovskite crystal structure 20 having a large area may be manufactured. Furthermore, the thickness of the perovskite crystal structure 20 may be easily adjusted by adjusting the distance between the substrate 100 and the flat portion 125 of the stamp 120. Furthermore, the kind of the substrate 100 used to manufacture the perovskite crystal structure 20 is not limited to a specific kind, and thus the single-crystalline perovskite crystal structure 20 may be easily manufactured on a desired substrate.

Evaluation results of characteristics of the perovskite crystal structure manufactured according to the aforementioned embodiments of the inventive concepts will be described hereinafter.

FIGS. 9 to 11 are scanning electron microscope (SEM) images of a surface and a cross section of a perovskite crystal structure manufactured according to some embodiments of the inventive concepts. In detail, FIG. 9 is a SEM image of a surface of a perovskite crystal structure according to some embodiments of the inventive concepts, which is measured on a scale of a millimeter or more. FIG. 10A and FIG. 10B show SEM images of a surface of a perovskite crystal structure according to some embodiments of the inventive concepts, which is measured on a scale of a micrometer or more. FIG. 11 is a SEM image of a cross section of a perovskite crystal structure according to some embodiments of the inventive concepts, which is measured on a scale of a micrometer or more.

$PbI_2$ (metal halogen compound) and $CH_3NH_3I$ (organic halogen compound) were mixed in dimethylformamide (DMF, solvent) to form a perovskite precursor solution having a concentration of 50%. The precursor solution was provided between a substrate and the stamp through the supply part of the stamp while the stamp rolled from a first region of the substrate to a second region of the substrate. Generation of a crystal nucleus on the first region of the substrate was observed, and a crystal was grown into the precursor solution provided on the second region of the substrate to manufacture a perovskite crystal structure (a width: 10 μm) according to some embodiments of the inventive concepts. To dry the precursor solution, the substrate was disposed on a hot plate and a temperature of the hot plate was maintained at 150 degrees Celsius or more. The perovskite crystal structure according to the embodiments of the inventive concepts was manufactured in about 2 minutes.

Detailed images of a surface and a cross section of the perovskite crystal structure manufactured according to the embodiments of the inventive concepts were measured using a scanning electron microscope (SEM).

Referring to FIGS. 9 and 10, the perovskite crystal structure in which regular patterns were formed was manufactured as shown in the SEM images of the surface of the perovskite crystal structure manufactured according to the embodiments of the inventive concepts.

Referring to FIG. 11, the perovskite crystal structure formed as a pattern on the substrate was manufactured as shown in the SEM image of the cross section of the perovskite crystal structure manufactured according to the embodiments of the inventive concepts.

As the results of FIGS. 9 to 11, as the stamp rolls on the substrate while rotating, the perovskite crystal structure according to the embodiments of the inventive concepts is not formed in contact portions of the substrate and the protrusion portions of the stamp. In addition, as the stamp rolls on the substrate while rotating, the substrate does not come in contact with the flat portion of the stamp. Thus, the precursor solution fills the space generated between the substrate and the flat portion of the stamp and is dried to manufacture the perovskite crystal structure according to the embodiments of the inventive concepts. As a result, the size of the space filled with the precursor solution is adjusted by the distance between the protrusion portions provided on the outer circumferential surface of the stamp and/or the distance between the flat portion and the substrate, and the thickness and the shape of the perovskite crystal structure according to the embodiments of the inventive concepts is determined by the space.

FIG. 12A and FIG. 12B show selected area electron diffraction (SAED) images of a perovskite crystal structure according to some embodiments of the inventive concepts. In detail, an image of FIG. 12A is a SAED image at an isolated position on a perovskite crystal structure according to some embodiments of the inventive concepts, and an image of FIG. 12B is a detailed SAED image at the isolated position on the perovskite crystal structure according to some embodiments of the inventive concepts.

A perovskite crystal structure according to some embodiments of the inventive concepts was manufactured by the same method as described with reference to FIGS. 9 to 11. Diffraction characteristics of an electron beam irradiated to the perovskite crystal structure were observed using a SAED apparatus to check a crystal structure of the perovskite crystal structure manufactured according to the embodiments of the inventive concepts.

Referring to the image FIG. 12A, the perovskite crystal structure manufactured according to the embodiments of the inventive concepts includes a portion in which the perovskite crystal structure is not formed, and a portion in which the perovskite crystal structure is formed. This may be because the perovskite crystal structure according to the embodiments of the inventive concepts is formed at a position isolated by the protrusion portions provided on the outer circumferential surface of the stamp. Reference numerals 1 to 4 and 5 to 8 illustrated in the image of FIG. 12A are crystal structures in the perovskite crystal structure formed at the position isolated by the protrusion portions provided on the outer circumferential surface of the stamp.

As shown in the image of FIG. 12B, the crystal structures are the same as each other in the perovskite crystal structure formed at the position isolated by the protrusion portions provided on the outer circumferential surface of the stamp. In addition, SAED spots clearly represent one crystal form.

As the results of FIG. 12A and FIG. 12B, it is recognized that the perovskite crystal structure according to the embodiments of the inventive concepts is manufactured at the position isolated by the protrusion portions provided on the outer circumferential surface of the stamp, i.e., in the limited space. In addition, the perovskite crystal structure formed at the isolated position has the same crystal structure. Furthermore, the SAED spots are clear and represent one crystal form, and thus the perovskite crystal structure manufactured according to the embodiments of the inventive concepts is single-crystalline.

FIG. 13 is an X-ray diffraction (XRD) graph of a perovskite crystal structure according to some embodiments of the inventive concepts.

A perovskite crystal structure according to some embodiments of the inventive concepts was manufactured by the same method as described with reference to FIGS. 9 to 11. An intensity according to X-ray diffraction of the perovskite crystal structure according to the embodiments of the inventive concepts was measured using an XRD apparatus.

Referring to FIG. 13, peaks of the X-ray diffraction intensity are prominently represented in (110) and (220) directions which are upward directions of the perovskite crystal structure according to the embodiments of the inventive concepts. Thus, the perovskite crystal structure according to the embodiments of the inventive concepts is grown in a (001) crystal direction corresponding to an upward direction.

FIG. 14 is a graph illustrating an XRD Φ-scan pattern of a perovskite crystal structure according to some embodiments of the inventive concepts.

A perovskite crystal structure according to some embodiments of the inventive concepts was manufactured by the same method as described with reference to FIGS. 9 to 11. An intensity according to X-ray diffraction of the perovskite crystal structure according to the embodiments of the inventive concepts was measured using an XRD apparatus, and then, an XRD Φ-scan pattern was extracted from the measured X-ray diffraction intensity.

Referring to FIG. 14, four-fold symmetry of the perovskite crystal structure according to the embodiments is checked. Thus, like the results of FIG. 12A and FIG. 12B, it is recognized that a crystal in a form symmetrical at 90 degrees to a side is grown in the perovskite crystal structure.

FIG. 15 is an XRD graph according to a thickness of a perovskite crystal structure according to some embodiments of the inventive concepts.

Perovskite crystal structures according to some embodiments of the inventive concepts were manufactured by the same method as described with reference to FIGS. 9 to 11. Here, the perovskite crystal structures were manufactured to have different thicknesses (i.e., 200 nm, 500 nm, and 1 μm) by changing a height of the stamp. Intensities according to X-ray diffraction of the perovskite crystal structures having the different thicknesses were measured using an XRD apparatus.

Referring to FIG. 15, peaks of the X-ray diffraction intensity are sharp at (110) and (220) directions in the XRD graphs of the perovskite crystal structures having the thicknesses of 200 nm and 500 nm. On the contrary, peaks are observed at other poly crystal directions such as (020), (123) and (130) directions as well as (110) and (220) directions in the XRD graph of the perovskite crystal structure having the thickness of 1 μm. Thus, it is recognized that a single-crystallinity is changed depending on the thickness of the perovskite crystal structure manufactured according to the embodiments of the inventive concepts. In other words, the single-crystallinity is adjusted by thickness of the perovskite crystal structure, and the single-crystallinity is significantly reduced when the thickness of the perovskite crystal structure is 1 μm or more.

FIG. 16 is an energy dispersive X-ray spectrometer (EDX) graph of a perovskite crystal structure according to some embodiments of the inventive concepts.

A perovskite crystal structure according to some embodiments of the inventive concepts was manufactured by the same method as described with reference to FIGS. 9 to 11. The perovskite crystal structure manufactured according to the embodiments of the inventive concepts was qualitatively analyzed using an EDX apparatus.

Referring to FIG. 16, the perovskite crystal structure manufactured according to the embodiments of the inventive concepts includes N, Pb, and I. This may be because the precursor solution used to manufacture the perovskite crystal structure is formed by mixing $PbI_2$ (the metal halogen compound) and $CH_3NH_3I$ (the organic halogen compound) in the DMF solvent. Qualitative analysis values of the perovskite crystal structure manufactured according to the embodiments of the inventive concepts are shown in the following table 1.

TABLE 1

| Element | Line type | k factor | Absorption correction | Wt % | Wt % sigma | Atomic % |
| --- | --- | --- | --- | --- | --- | --- |
| N | K series | 3.69981 | 1.00 | 2.41 | 1.08 | 20.47 |
| I | L series | 2.00294 | 1.00 | 64.47 | 1.45 | 60.49 |
| Pb | L series | 1.67913 | 1.00 | 33.13 | 1.31 | 19.04 |
| Total | | | | 100.00 | | 100.00 |

Since the perovskite crystal structure according to the embodiments of the inventive concepts is $CH_3NH_3PbI_3$, an atomic ratio of the perovskite crystal structure according to the embodiments is theoretically N:I:Pb=1:3:1. Referring to the table 1, the perovskite crystal structure according to the embodiments of the inventive concepts includes N having an atomic percent of 20.47%, I having an atomic percent of 60.49%, and Pb having an atomic percent of 19.04%. The atomic percent of N, I and Pb in the table 1 are similar to the theoretical atomic percent.

FIG. 17 is a 2D XRD result graph of a perovskite crystal structure according to some embodiments of the inventive concepts.

A perovskite crystal structure according to some embodiments of the inventive concepts was manufactured by the same method as described with reference to FIGS. 9 to 11, and the perovskite crystal structure manufactured according to the embodiments was analyzed using a 2-dimensional XRD apparatus.

Referring to FIG. 17, the perovskite crystal structure according to the embodiments of the inventive concepts has analysis results matching with the measured results described with reference to FIGS. 12 to 15 and has a single-crystalline structure having substantially the same crystal face.

FIG. 18 is a high-resolution transmission electron microscopy (TEM) image of a perovskite crystal structure according to some embodiments of the inventive concepts.

A perovskite crystal structure according to some embodiments of the inventive concepts was manufactured by the same method as described with reference to FIGS. 9 to 11. An image of the perovskite crystal structure manufactured according to the embodiments was obtained using a high-resolution TEM apparatus, and lattice structures of a crystal face of the perovskite crystal structure were observed.

Referring to FIG. 18, the lattice structures are substantially the same as each other in the crystal face of the perovskite crystal structure manufactured according to the embodiments of the inventive concepts, and a lattice distance is 0.31 nm. The lattice distance of 0.31 nm is a result matching with a (004) plane of perovskite, and thus the perovskite crystal structure manufactured according to the embodiments is a substantially single-crystalline perovskite crystal structure.

FIG. 19A and FIG. 19B show SEM images for explaining crystallization of a perovskite crystal structure according to some embodiments of the inventive concepts.

Perovskite crystal structures having different widths (100 nm and 600 nm), according to some embodiments of the inventive concepts, were manufactured by the same method as described with reference to FIGS. 9 to 11. Thereafter, SEM images of the perovskite crystal structures having the different widths were obtained.

Referring to FIG. 19A and FIG. 19B, an image of FIG. 19A is the SEM image of the perovskite crystal structure having the width of 100 nm, and an image of FIG. 19B is the SEM image of the perovskite crystal structure having the width of 600 nm.

When the width of the perovskite crystal structure is 10 μm like the embodiments of FIGS. 12 to 15, the perovskite crystal structure has the substantially single-crystalline structure. In addition, even though the width of the perovskite crystal structure is 100 nm or 600 nm, the perovskite crystal structure has a substantially single-crystalline structure as shown in FIG. 19A and FIG. 19B. In other words, the perovskite crystal structure according to the embodiments of the inventive concepts may be manufactured in various shapes such as a nano-line shape or a film shape so as to be applied to various applications.

According to the aforementioned embodiments of the inventive concepts, the perovskite precursor solution may be provided into the limited space between the substrate and the stamp while the stamp rolls from the first region to the second region of the substrate, and then, the precursor solution provided in the limited space may be dried to manufacture the single-crystalline perovskite crystal structure. The limited space may be adjusted by the protrusion portions provided on the outer circumferential surface of the stamp, and the thickness of the perovskite crystal structure according to the embodiments of the inventive concepts may be easily adjusted by adjusting the distance from the substrate to the flat portion disposed between the protrusion portions of the stamp. The method for manufacturing the single-crystalline perovskite crystal structure, which is capable of reducing the process time and the process cost and of providing the large area, may be realized using the simple process of drying the precursor solution after supplying the precursor solution into the limited space through the stamp.

In the experimental embodiments described above, the single-crystalline structure was manufactured using the perovskite. However, embodiments of the inventive concepts are not limited thereto. The technical features according to the embodiments of the inventive concepts may be applied to various materials.

The method for manufacturing the perovskite crystal structure and the apparatus for manufacturing the perovskite crystal structure therefor, according to the embodiments of the inventive concepts, may be used in various industrial fields such as solar cells, laser, optical sensors, light emitting devices, and transistors.

According to some embodiments of the inventive concepts, the method for manufacturing a perovskite crystal structure may include preparing a substrate, disposing a stamp having a roll shape on the substrate, injecting a perovskite precursor solution between the substrate and the stamp, and drying the precursor solution to manufacture a perovskite crystal structure. The stamp may include protrusion portions on an outer circumferential surface of the stamp, and a flat portion between the protrusion portions. The stamp may roll in a first direction on the substrate, and the precursor solution may be continuously crystallized in the first direction between the substrate and the stamp to manufacture the perovskite crystal structure.

According to some embodiments of the inventive concepts, a large-area single-crystalline perovskite crystal structure may be manufactured using the solution process (or the liquid process).

In addition, the process time and the process cost may be reduced through the simple process of drying the precursor solution after supplying the precursor solution into the limited space by the stamp. Furthermore, the thickness of the perovskite crystal structure may be easily adjusted by adjusting the distance between the substrate and the flat portion of the stamp.

While the inventive concepts have been described with reference to exemplary embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. A method for manufacturing a perovskite crystal structure, the method comprising:
    preparing a substrate;
    disposing a stamp having a roll shape on the substrate;
    injecting a perovskite precursor solution between the substrate and the stamp; and
    drying the precursor solution to manufacture a perovskite crystal structure,
    wherein the stamp rolls in a first direction on the substrate, and
    wherein the precursor solution is continuously crystallized in the first direction between the substrate and the stamp to manufacture the perovskite crystal structure.

2. The method of claim 1, wherein the stamp rolls from a first region of the substrate to a second region of the substrate while rotating about a rotation axis parallel to a second direction perpendicular to the first direction.

3. The method of claim 2, wherein the precursor solution is supplied onto an outer circumferential surface of the stamp, and
    wherein the precursor solution flows along the outer circumferential surface of the stamp so as to be injected between the substrate and the stamp.

4. The method of claim 3, wherein a crystal nucleus is generated earlier in the precursor solution provided on the first region of the substrate than in the precursor solution provided on the second region of the substrate.

5. The method of claim 4, wherein the drying of the precursor solution comprises: generating a crystal from the precursor solution and removing a solvent from the precursor solution, by a heating process.

6. The method of claim 5, wherein the stamp comprises: protrusion portions which are provided on the outer circumferential surface and have loop shapes surrounding the outer circumferential surface.

7. The method of claim 6, wherein the outer circumferential surface of the stamp includes a flat portion between the protrusion portions, and
    wherein the precursor solution fills a space between the protrusion portions and between the substrate and the flat portion.

8. The method of claim 7, wherein the space filled with the precursor solution is adjusted by a distance between the protrusion portions arranged in the second direction on the outer circumferential surface of the stamp and is adjusted by a distance between the flat portion and the substrate in a third direction perpendicular to the first and second directions.

9. The method of claim 8, wherein a thickness of the perovskite crystal structure formed between the substrate and the flat portion of the stamp is greater than a thickness of the perovskite crystal structure formed between the substrate and the protrusion portion of the stamp.

10. The method of claim 9, wherein a thickness of the perovskite crystal structure is determined depending on the distance between the substrate and the flat portion of the stamp.

11. The method of claim 1, wherein a single-crystallinity of the perovskite crystal structure is adjusted by adjusting a thickness of the perovskite crystal structure.

12. The method of claim 1, wherein the perovskite crystal structure is a single crystal.

13. An apparatus for manufacturing a perovskite crystal structure, the apparatus comprising:
    a substrate;
    a stamp having a roll shape on the substrate; and
    a supply part for supplying a perovskite precursor solution onto an outer circumferential surface of the stamp,
    wherein the stamp rolls from a first region of the substrate to a second region of the substrate, and
    wherein the stamp comprises: protrusion portions which are provided on the outer circumferential surface and have loop shapes surrounding the outer circumferential surface; and a flat portion between the protrusion portions,
    wherein the protrusion portions are separated from each other in a length direction of the stamp.

14. The apparatus of claim 13, wherein the supply part moves while supplying the precursor solution onto the outer circumferential surface of the stamp, along a direction in which the stamp rolls from the first region to the second region of the substrate.

15. The apparatus of claim 14, wherein the precursor solution provided on the substrate is crystallized in a direction from the first region toward the second region.

16. A method for manufacturing a crystal structure, the method comprising:
    providing a precursor solution on a substrate; and
    drying the precursor solution to manufacture a crystal structure,
    wherein the precursor solution is continuously crystallized from a first region of the precursor solution to a second region of the precursor solution, and
    wherein a single-crystallinity of the crystal structure is adjusted depending on a thickness of the precursor solution.

17. The method of claim 16, wherein the first region of the precursor solution is provided on the substrate prior to the second region of the precursor solution.

18. The method of claim 16, wherein the precursor solution includes a perovskite precursor solution.

19. The method of claim 16, wherein the crystal structure is a single crystal.

* * * * *